United States Patent
Hopper et al.

(10) Patent No.: US 10,317,564 B2
(45) Date of Patent: Jun. 11, 2019

(54) NON-RESONANT LOGGING TOOLS

(71) Applicant: Schlumberger Technology Corporation, Sugar Land, TX (US)

(72) Inventors: Timothy Andrew John Hopper, Subiaco (AU); David G Cory, Branchton (CA); Julius Kusuma, Arlington, MA (US); Yi-Qiao Song, Newton Center, MA (US); Martin D. Hurlimann, Newton, MA (US); Martin E. Poitzsch, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/479,318

(22) Filed: Apr. 5, 2017

(65) Prior Publication Data
US 2017/0205528 A1  Jul. 20, 2017

Related U.S. Application Data

(62) Division of application No. 13/150,871, filed on Jun. 1, 2011, now Pat. No. 9,632,203.

(60) Provisional application No. 61/357,312, filed on Jun. 22, 2010, provisional application No. 61/357,833, filed on Jun. 23, 2010.

(51) Int. Cl.
*G01V 3/00* (2006.01)
*G01V 3/32* (2006.01)
*G01N 24/08* (2006.01)
*G01R 33/36* (2006.01)

(52) U.S. Cl.
CPC .............. *G01V 3/32* (2013.01); *G01N 24/081* (2013.01); *G01R 33/3607* (2013.01); *G01R 33/3621* (2013.01)

(58) Field of Classification Search
CPC .......................................................... G01V 3/32
USPC ........................................ 324/303, 318, 322
See application file for complete search history.

(56) References Cited

U.S. PATENT DOCUMENTS

| | | | |
|---|---|---|---|
| 4,791,392 A | 12/1988 | Brunner et al. | |
| 5,435,302 A | 7/1995 | Lenkinski et al. | |
| 5,804,967 A * | 9/1998 | Miller | G01R 33/441 324/307 |
| 6,002,256 A * | 12/1999 | Slade | G01R 33/3614 324/318 |
| 6,107,797 A | 8/2000 | Sezginer | |
| 6,133,735 A | 10/2000 | Hurlimann et al. | |

(Continued)

FOREIGN PATENT DOCUMENTS

EP   0823639 A1   2/1998

OTHER PUBLICATIONS

Walsh. Multi-channel NMR Surface Instrumentation and Software for 1D/2D Groundwater Investigations. Journal of Applied Geophysics, vol. 66, pp. 140-150, 2008.

(Continued)

*Primary Examiner* — Louis M Arana

(57) ABSTRACT

Methods and systems are provided for tools having non-resonant circuits for analyzing a formation and/or a sample. For example, nuclear magnetic resonance and resistivity tools can make use of a non-resonant excitation coil and/or a detection coil. These coils can achieve desired frequencies by the use of switches, thereby removing the requirement of tuning circuits that are typical in conventional tools.

17 Claims, 9 Drawing Sheets

(56) References Cited

U.S. PATENT DOCUMENTS

| | | | |
|---|---|---|---|
| 6,166,543 | A | 12/2000 | Sezginer et al. |
| 6,366,086 | B1 | 4/2002 | Sen |
| 6,777,940 | B2 | 8/2004 | Macune |
| 7,362,182 | B2 | 4/2008 | Barabash et al. |
| 7,859,260 | B2 | 12/2010 | Reiderman |
| 7,986,143 | B2 | 7/2011 | Walsh |
| 8,269,498 | B2 * | 9/2012 | Zhang ............... G01R 33/3628 324/318 |
| 8,754,647 | B2 | 6/2014 | Van Helvoort et al. |
| 9,057,767 | B2 * | 6/2015 | Hadley ............. G01R 33/3415 |
| 9,632,203 | B2 * | 4/2017 | Hopper ................... G01V 3/32 |
| 2004/0090234 | A1 | 5/2004 | Macune |
| 2004/0257241 | A1 | 12/2004 | Menger |
| 2006/0255799 | A1 | 11/2006 | Reiderman |
| 2012/0001629 | A1 | 1/2012 | Hopper et al. |
| 2012/0098542 | A1 | 4/2012 | Van Helvoort et al. |
| 2013/0088234 | A1 * | 4/2013 | Ham .................. G01R 33/3852 324/322 |

OTHER PUBLICATIONS

Lowe et al. A fast recovery pulsed nuclear magnetic resonance sample probe using a delay line. AIP Review of Scientific Measurements. 45, 631. 1974.

Kubo et al., Ultra-broadband NMR probe: numerical and experimental study of transmission line NMR probe. JMR 162, 284-299. 2003.

Murphree et al., An easily constructed, tuning free, ultra-broadband probe form NMR. JMR 1088. 160-167. 2007.

\* cited by examiner

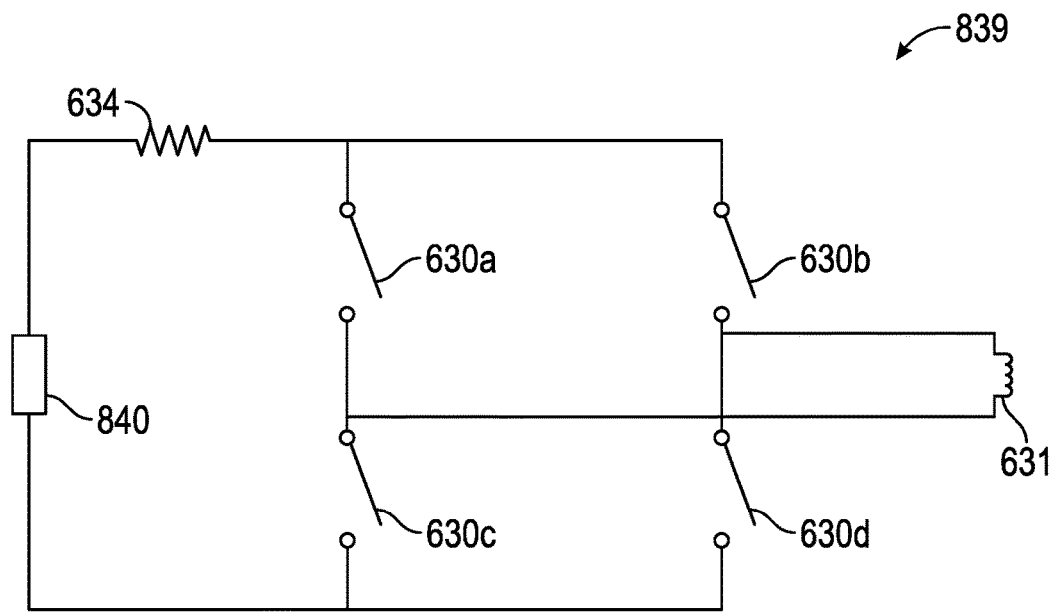
FIG. 8
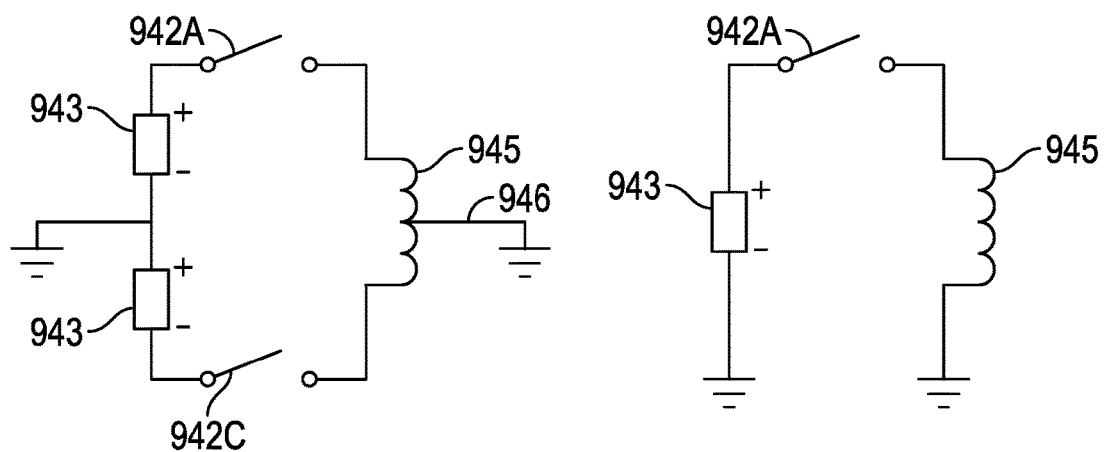
FIG. 9     FIG. 10

NON-RESONANT LOGGING TOOLS

CROSS-REFERENCE TO RELATED APPLICATIONS

This application is a divisional application of U.S. patent application Ser. No. 13/150,871, filed on Jun. 1, 2011, which claims priority to and the benefit of, U.S. Provisional Application Nos. 61/357,312, filed on Jun. 22, 2010, and 61/357,833, filed on Jun. 23, 2010, all of which are incorporated herein by reference.

TECHNICAL FIELD

The invention relates generally to the field of logging a borehole or measuring a sample. More specifically, the invention relates to obtaining nuclear magnetic resonance (NMR) and/or resistivity measurements of formations or samples with the use of at least one non-resonant circuit.

BACKGROUND

Conventional nuclear magnetic resonance (NMR) tools and conventional resistivity tools can be used in a variety of applications from downhole logging to analysis of samples in a lab, in refineries, for food and chemical processing, and the like. These conventional tools often make use of a resonant circuit to cause an excitation signal necessary to perform the appropriate measurements. The use of resonant circuits can cause certain difficulties and restrictions in conventional resistivity and NMR tools alike.

For example, today's common approach to the excitation and detection system for resistivity logging is to employ a tuned resistor-inductor-capacitor (RLC) circuit for both excitation and detection. When logging at a multitude of frequencies is required, as it is in most cases, then the circuits have to be tuned to have peaks at multiple frequencies. The multi-tuning process is labor-intensive, and further it is known that the tuning changes with temperature and may drift to the point that it is hurtful to the measurement. When the number of resonant frequencies is large (generally three or above), then a selector switch can be used to select between several circuits with different tunings. In some cases, this selector switch itself becomes a weak point in the design.

In such a circuit, each resonant peak in frequency is completely characterized by three parameters: the resonance frequency, the impedance on resonance, and the quality factor. For a circuit with a reasonable quality factor (~100) the resonance frequency acts to efficiently couple the energy contained in the coil during excitation to the formation and to reject noise at frequencies outside of the resonance bandwidth during detection. Both of these features are essential elements to maintaining system performance at high resonance frequencies. At low resonance frequencies there is another approach to achieving the same efficiencies based on switching technologies.

Various challenges exist with respect to the use of tuned circuits in well logging. For example, there is variation of the magnetic field with temperature, mud loading, and formation loading. The Q of the circuit is a measure of the ratio of the stored to dissipated energy in the circuit. When the temperature of the coil changes (as with formation depth) the Johnson noise in the circuit changes and the Q changes in response. When the resistivity of the material in the field of the tool changes (either from variations in mud or formation fluids) the Q changes in response. These changes lead to miss-settings of the resistivity parameters and variations in the observed signal intensity and derived relaxation times. Left uncompensated, changes in Q degrade instrument performance.

There are also limitations in the number of frequencies for which a given tuned circuit can be tuned to. In some cases this necessitates the use of several tuned circuits, each tuned to a possibly different set of frequencies.

In the situation where the resonance frequency is low (<1 MHz), tools with reasonable Qs ring. The tuned circuit acts as a bell and having driven the circuit with a few hundred to a thousand volts, waiting is necessary until the natural response decays to of order tens of micro-volts before acquiring a signal. Additionally, it is appealing to run the logging tool at multiple-depths to help characterize the formation. With the resonant approach changing depth is accomplished by changing the resonance frequency, which demands a change in the tuning and in the electronics.

Finally, the characteristic of the formation may require a different setting to be used (for example in terms of frequency of excitation signal). Pre job modeling and planning attempts to select the best settings for the LWD tool, but changing formation characteristics can present a significant uncertainty. Also, for complex formations it may be desirable to be able to change the settings of the LWD tool from one time to another. Hence, flexible hardware is highly desirable.

Similar issues arise with respect to conventional downhole NMR tools. Conventional NMR tools commonly use metallic wire wound coils to excite nuclear spins by passing an RF current and generating an RF magnetic field, and to detect the nuclear spin magnetization by receiving the electric current induced in the coil. In order to achieve efficient coupling of this coil and the rest of the electronics, this coil is often connected with a capacitor in parallel to form a resonance circuit. Such a parallel circuit is known to be resonant at a frequency f0:

$$f_0 = \frac{1}{2\pi(LC)^{1/2}}$$

where L is the inductance of the coil and C is a capacitance of the capacitor. This frequency f0 is called the resonance frequency.

For conventional NMR circuits, this resonance frequency is adjusted by the choice of the capacitor to match the value of the Larmor frequency of spin precession for a given magnetic field. For example, at a magnetic field of 1 Tesla, the Larmor frequency of a hydrogen atom is 42.58 MHz. A second capacitor is often used to adjust the impedance of this resonance circuit to match the impedance (e.g. 50 ohm) of the power amplifier and receiver. It is a common practice that all subsystems (coil system, receiver, and power amplifiers, and cables) are selected or tuned to be 50 ohm, even though other values of the impedance have been used. Although the exact value of the impedance can be a matter of choice, the impedance matching is important for efficient power transmission to the coil to achieve good RF B1 field and also optimal receiver sensitivity.

In practice, variable capacitors are often used to adjust the resonance frequency (tuning) and the impedance (matching). Both tuning and matching conditions can vary during an experiment due to component drift, changes in temperature and sample properties. An NMR experimentalist needs to adjust frequently either capacitors to maintain a good matching and tuning condition. A poorly adjusted tuning and matching condition can lead to deterioration of signal, poor control of spin dynamics and unwanted signals.

One embodiment disclosed herein is a novel method to couple the coil to the NMR electronics without the need to tune the coil system to a resonant frequency at the Larmor frequency. The coil may be connected to the RF electronics directly or through electronics switches and the response of such a system can be much more broadband than a conventional resonance coil system. The main benefit of such system is that there may be no need for the tuning and matching capacitors and no need to adjust the circuit during NMR experiments and for different samples. This method is particularly useful for NMR at low frequency or when the coil inductance is very low, so that the impedance of the coil at the Larmor frequency (2pi*f0*L) is small.

For NMR applications in oilfield exploration such as NMR logging and LWD NMR logging, this new approach can eliminate the need to adjust the tuning capacitors and the associated relays and other electronics and greatly improve the robustness of these logging systems. The system will also be more stable under different conditions, such as different sample or environmental salinity and different fluids.

The science and technology of NMR involves two main aspects. One is the science of the nuclear spin system and the use of magnetic fields to control their behavior and dynamics. The essential phenomenon of NMR is the resonant absorption and irradiation of RF energy by the nuclear spins in a static magnetic field, B0. The frequency of the irradiation is called Larmor frequency, f=gamma*B0, where gamma is the gyromagnetic ratio specific to each element. For example, a commonly used nucleus for NMR is proton with a gamma=4258 Hz/G. The applied magnetic fields are often of two kinds. One is the static field that determines the Larmor frequency. The second is RF irradiation at this Larmor frequency. It is used to perform spin rotation.

The second part of the NMR is the associated electronics to (1) apply the RF irradiation at the Larmor frequency to the spin system and samples in order to control the behavior and dynamics of the spins; and (2) to receive the spin precession signals. One design goal of such electronics is the efficient transmission of RF power to the sample region in order to achieve control of the spin system. The tuning circuit is well suited for such power transmission. For example, assuming the power amplifier and the circuit are tuned to a common impedance of 50 ohm, then the maximum of the power from the amplifier will be delivered to the circuit. Since the capacitors are often of higher quality factor than the coil, the applied power is dissipated in the coil resistance to produce the maximum electrical current and in turn the maximum RF B1 magnetic field. However, if the impedance of the coil system is significantly different from that of the amplifier, less power will be deposited in the coil and thus less optimal B1 field.

In addition to the efficient transmission of the RF power and efficient signal reception from the matched impedance, the resonance circuit also behaves as a band-pass filter centered at the resonance frequency. The width of the bandwidth is controlled by the resistance of the circuit, often dominated by that of the coil. The ratio of the resonance frequency and the width of the resonance is often called the Q factor. For common NMR circuits, Q is often on the order of 100. Only the signals within the bandwidth of the circuit are effectively coupled to the output electronics. Signals outside the bandwidth are attenuated. The tuned coil acts as a narrow band filter.

To summarize, in a conventional NMR system, there are two resonance phenomena. One is the resonant absorption of the spin system of the RF energy and the resonant manipulation of the spin system by the RF pulses. The frequency of this resonance is determined by the externally applied magnetic field and the choice of the nuclei to be interrogated. The second resonance is the electronics and circuit of the NMR equipment to supply the RF pulses and to detect NMR signal. The conventional NMR circuit using resonance circuit can be an excellent circuit to achieve efficient transmission and reception. Certain embodiments disclosed herein include an alternative method for the NMR circuit that does not require a resonant condition. This will enable a more broadband transmission of RF pulses and reception of NMR signals.

Thus, needs in the art exist for systems and methods that address some of the deficiencies in conventional tools, such as some of the deficiencies described above.

BRIEF DESCRIPTION OF THE DRAWINGS

FIG. 8 is a schematic of an H-bridge for use in a non-resonant NMR logging tool, according to an example embodiment.

FIG. 9 is a schematic of a circuit for use in a non-resonant NMR logging tool, according to an example embodiment.

FIG. 10 is a schematic of a circuit for use in a non-resonant NMR logging tool, according to an example embodiment.

DETAILED DESCRIPTION OF THE EXAMPLE EMBODIMENTS

Some embodiments will now be described with reference to the figures. Like elements in the various figures will be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship as appropriate.

Figure 1:
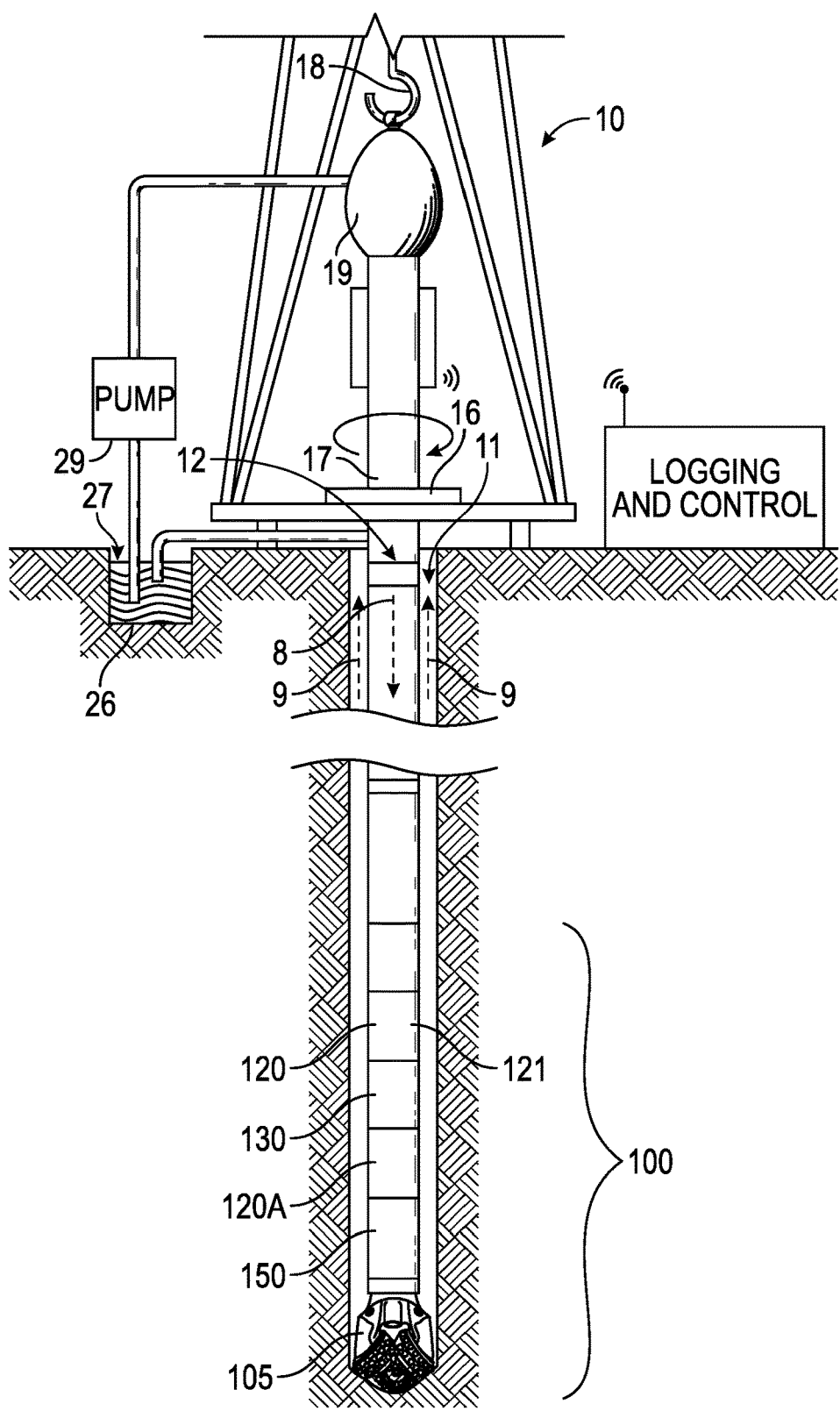
FIG. 1 illustrates a wellsite system, according to an example embodiment.

FIG. 1 illustrates a wellsite system, according to an example embodiment. The wellsite can be onshore or offshore. In this example system, a borehole 11 is formed in subsurface formations 106 by rotary drilling in a manner that is well known. Embodiments of the invention can also use directional drilling, as will be described hereinafter.

A drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, Kelly 17, hook 18 and rotary swivel 19. The drill string 12 is rotated by the rotary table 16, energized by means not shown, which engages the Kelly 17 at the upper end of the drill string. The drill string 12 is suspended from a hook 18, attached to a travelling block (also not shown), through the Kelly 17 and a rotary swivel 19 which permits rotation of the drill string relative to the hook. As is well known, a top drive system could alternatively be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole 11, as indicated by the directional arrows 9. In this well known manner, the drilling fluid lubricates the drill bit 105 and carries formation 106 cuttings up to the surface as it is returned to the pit 27 for recirculation.

In various embodiments, the systems and methods disclosed herein can be used with any means of conveyance known to those of ordinary skill in the art. For example, the systems and methods disclosed herein can be used with tools or other electronics conveyed by wireline, slickline, drill pipe conveyance, coiled tubing drilling, and/or a while-drilling conveyance interface. For the purpose of an example only, FIG. 1 depicts a while-drilling interface. However, systems and methods disclosed herein could apply equally to wireline or any other suitable conveyance means. The bottom hole assembly 100 of the illustrated embodiment includes a logging-while-drilling (LWD) module 120, a measuring-while-drilling (MWD) module 130, a roto-steerable system and motor, and drill bit 105.

The MWD module 130 is housed in a drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

The LWD module 120 is also housed in a drill collar, as is known in the art, and can contain one or a plurality of known types of logging tools (e.g., logging tool 121). It will also be understood that more than one LWD and/or MWD module can be employed, e.g. as represented at 120A. (References, throughout, to a module at the position of 120 can alternatively mean a module at the position of 120A as well.) The LWD module includes capabilities for measuring, processing, and storing information, as well as for communicating with the surface equipment.

Figure 2:
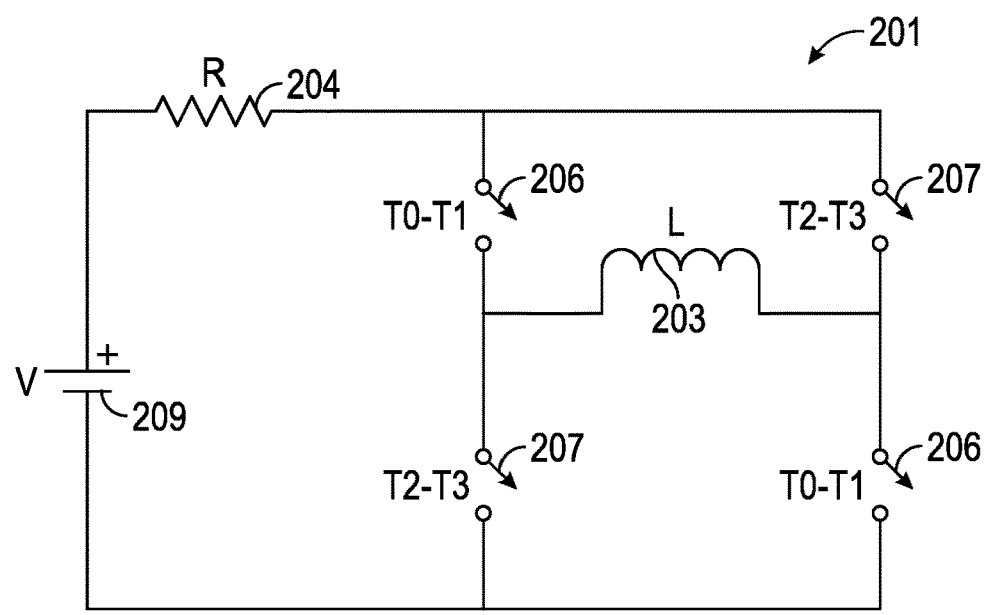
FIG. 2 is a diagram of an H-bridge circuit used in a resistivity logging tool having a non-resonant system, according to an example embodiment.

The tool 121 of FIG. 1 can, in various embodiments, include a variety of logging tools. In an example embodiment, the tool 121 can be a resistivity logging tool having a non-resonant system. A non-resonant system can use an un-tuned coil. That is, no tuning capacitor need be used. Instead, the frequency of excitation is achieved by the use of fast MOSFET switches. In some embodiments, these switches need to be able to switch at the frequencies of the desired excitation. Additionally, in some embodiments, the switches need to be able to handle high current and have a fast recovery time. The transmit power can come from a DC source—the aim being to put in as much power in a short period of time into each side of a switching network such as an H-bridge. FIG. 2 is a diagram of an H-bridge circuit 201 used in a resistivity logging tool having a non-resonant system, according to an example embodiment. FIG. 2 shows a basic design of the switching network being an H-bridge 201 with the coil in the middle drive as a bipolar flux source from a single voltage source 209.

In the illustrated embodiment, the top half of the bridge 201 (switch t0-t1) 206 is fired with the switch on at time t0 and the switch off at time t1. The rise time of this is given by the time Tr=L/R, where L is the inductance of the inductor 203 and R is the resistance of the resistor 204 placed in series with the switches 206,207. The aim being to get as much current in as possible before the switch 206 is turned off. There is some recovery time allowed before the second half of the bridge 201 (t2-t3) 207 is switched on. The total time of this (to+t3+recovery) is the period of the pulse. The inverse of this is the frequency of the excitation. It is a broadband pulse, however, most of the energy is at the switching frequency. By varying the pulse lengths and hence, the total period, the frequencies can be changed. Thus, the system can be controllable by software, and multiple frequencies can be obtained by the same system with only a timing change. There need not be tuning or matching capacitors involved in the system. As mentioned previously, this high flexibility allows the LWD tool to have a very large number of possible settings, which can be changed during operations. Spin dynamics calculations, recognized by those skilled in the art having benefit of the present disclosure, have been used to determine the number of pulses required to tip the spins by any required angle.

In an example embodiment, detection can be achieved using the same coil as the transmit coil. In such an embodiment—where the same coil is used—the detection is non-resonant, in the same way that the excitation is non-resonant. In example embodiments, the receiver can be either switched on or switched off. The switches in this case can be used to protect the pre-amplifier from the high power transmitter pulses. The received signal is broadband and to achieve the same degree of noise rejection yielded from a tuned coil, a digital filter (e.g., Chebychev filter) can be used. This digital filter can be applied when there is enough dynamic range on the receiver. Essentially, the noise rejection is shifted from being achieved using an analog (tuned coil) system to a fully digital system. In some embodiments, the gain required in the digital system must make up for that lost from using the analog system.

In some embodiments, detection can be realized using a separate receiver coil. If such a second, separate coil is used, then it can be a tuned coil or an untuned coil. It will be possible to use a series of tune and matching circuits to vary the frequency of this to match the desired excitation frequency, as may be recognized by one of ordinary skill in the art having benefit of the present disclosure. Hence, the non-resonant excitation can still be used for multiple frequencies.

Figure 3:
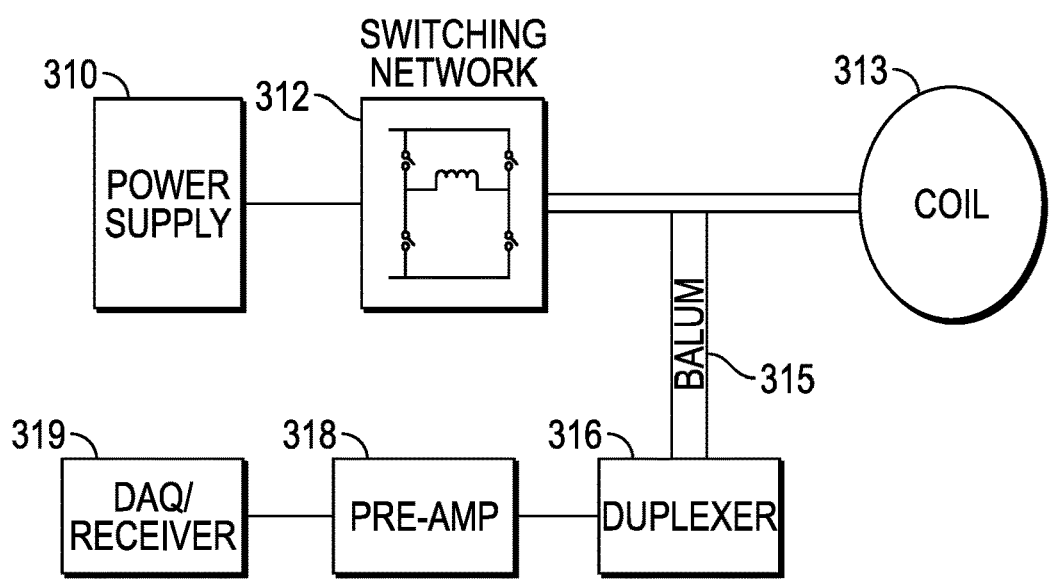
FIG. 3 is a schematic diagram of a system with non-resonant excitation and non-resonant detection for use with a resistivity logging tool, according to an example embodiment.

FIG. 3 is a schematic diagram of a system with non-resonant excitation and non-resonant detection for use with a resistivity logging tool, according to an example embodiment. As shown in FIG. 3, an example system can include a power supply 310 in communication with a switching network 312, which can be identical to or similar to the H-bridge 201 switching network described above with reference to FIG. 2. The switching network 312 then can operate to switch at frequencies of the desired excitation and detection, thereby enabling the coil 313 (which functions both as a transmitter and a receiver) to transmit and receive at the desired frequency. The coil 313 can also be in communication with a duplexer 316 through a balun transformer 315, the duplexer 316 then being in communication with a pre-amplifier 318 and DAQ/receiver 319.

Figure 4:
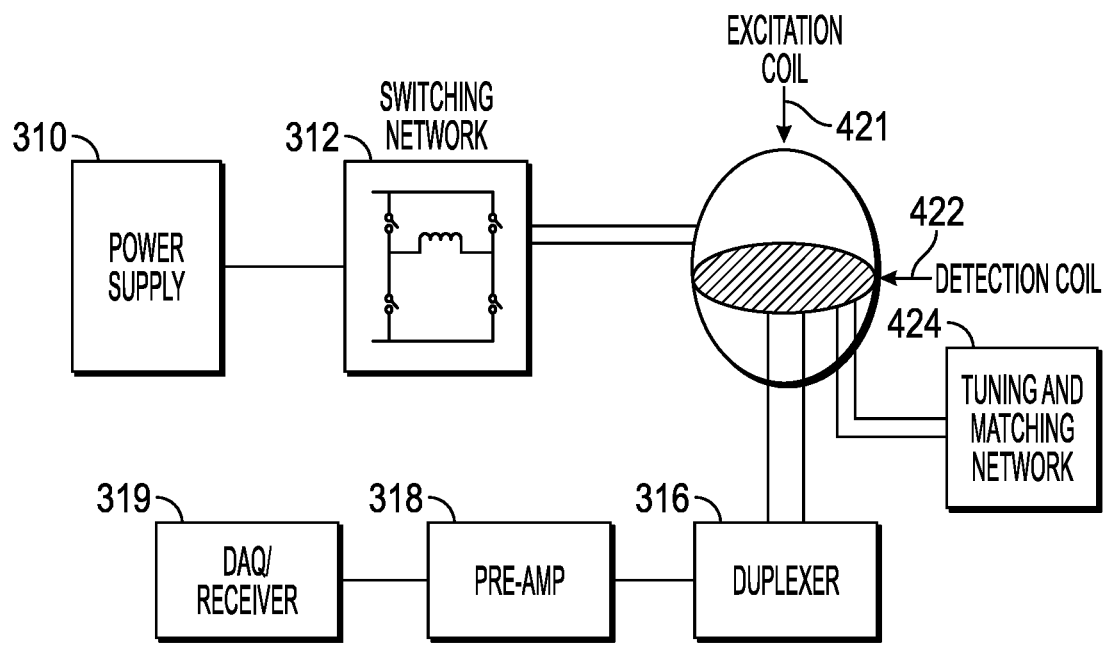
FIG. 4 is a schematic diagram of a system with non-resonant excitation and resonant detection for use with a resistivity logging tool, according to an example embodiment.

FIG. 4 is a schematic diagram of a system with non-resonant excitation and resonant detection for use with a resistivity logging tool, according to an example embodiment. As shown in FIG. 4, an example system of non-resonant excitation and resonant detection can include many of the same components described above with reference to FIG. 3—namely, a power supply 310, switching network 312, duplexer 316, pre-amplifier 318, and DAQ/receiver 319. These components can perform similar functions as in the system shown in FIG. 3. A principal difference between the systems of FIG. 3 and FIG. 4 is that the latter system includes separate excitation 421 and detection coils 422. The excitation coil is in communication with the switching network 312, which controls the frequency of the excitation coil 421, while the detection coil 422 is in communication with a tuning and matching network 424 that controls the frequency thereof.

As discussed previously, non-resonant circuits can be used with NMR logging tools as well as resistivity logging tools. In certain example embodiments described herein, the present disclosure describes various example components of systems comprising a non-resonant, pulsed NMR circuit with a coil.

As an example, the inductance and magnetic field of an NMR coil of 10 cm diameter (d) and length (L), made with 10 turns of conductive wire, is calculated. The equation for long solenoid as an approximation will be used. The magnetic field at the center of the coil is $$B1=\mu n I,$$

where $\mu$ is the permeability of air ($\mu=4\pi*10^{\wedge}(-7)$), n is the turn density (n=10/cm), and I is the current in the wire. For I=1 A, B1=0.0013 T=13 G. And the inductance of the coil $$L=\mu N^2 A^2/L,$$

where N is the total turns, A is the cross-section area. For the above coil, L=3 µH. Thus, at a Larmor frequency of 1 MHz, the impedance of the coil is dominated by the inductance, $Y=\omega L \sim 10$ ohm. Thus the voltage needed to drive a current of 1 A is about 10 volts. The formulae used in this example are crude since the coil may not be adequately long, but they illustrate the order of magnitude of the problem and show that such a coil can be easily powered by a conventional power amplifier without the need for a resonance circuit.

This example shows that NMR electronics can be directly coupled to the coil alone without the help of the resonance circuit for impedance matching. This is particularly true for NMR at relatively low frequency, such as 1 MHz or lower. At much higher frequencies, such as 800 MHz, the impedance of the coil inductance may become larger, which could conceivably make it more difficult to directly couple the power electronics without the impedance matching circuit such as a resonance circuit system.

In addition to very low field NMR, high field NMR using very small sample usually requires correspondingly small coils to achieve efficient coupling between the coil and sample, i.e. to improve filling factor. The inductance of such small coils can be very low. In fact, in order to tune such small coils (often called microcoil) to the Larmor frequency, a second large coil is often used to increase the inductance. Since no NMR signal is generated by the large coil, such a circuit may suffer from reduced signal-to-noise because the large coil can be a source of noise. Thus, microcoil NMR may also benefit from the non-resonance NMR circuit.

A non-resonant (NR) approach to NMR circuit is to perform NMR measurement with a coil but without resonance condition for the electronic circuit at the Larmor frequency. NR NMR has the potential to make NMR instruments (including wire-line and LWD NMR tools) more robust and more versatile. It replaces the properties of an analog tuned circuit (for impedance matching and band filtering) for the versatility of a digital pulsed circuit. This new concept is possible today at due to improvements in fast switching electronics. As may be recognized by one of ordinary skill in the art having benefit of the present disclosure, with other technological advancements such as the improvement of the speed of switching electronics over time, higher and higher resonance frequencies may be easily accomplished through NR NMR.

Figure 5:
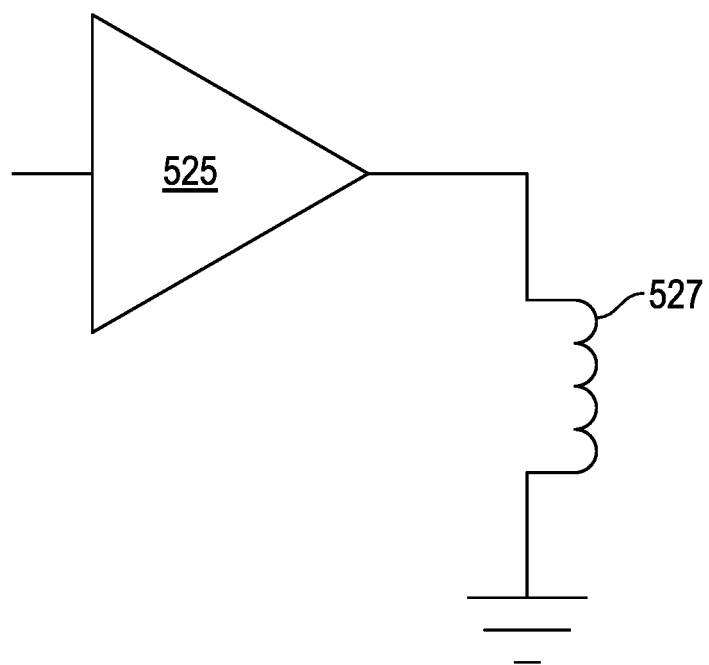
FIG. 5 is a schematic of an RF power amplifier directly connect to a coil, according to an example embodiment.

Below is demonstrated a few systems and methods for using and building NR NMR circuits according to certain example embodiments. There are two example ways to couple the RF power system into an untuned coil disclosed herein. FIG. 5 is a schematic of an RF power amplifier directly connect to a coil, according to an example embodiment. The coil can behave as an inductor.

The power amplifier 525 can be of any class (e.g. A, B, AB and D). The RF pulses and power can be delivered to the coil 527 directly. Discrete components, such as a resistor, inductor or a capacitor, cross-diodes, or any other control element, can be added to limit the current supply, for noise cancelation purpose, or for an improved impedance matching. However, there is no need to use capacitors and other inductors to form a resonance circuit at the Larmor frequency. In an example embodiment, the timing of switches put the power into the coil 527 at precise times, and this discrete timing, sets up the 'frequency' of excitation. The power amps may have to go through the H-bridge. In another example embodiment, such as in the case of no switches and no tuning elements, a coil may resonate at its own self resonance frequency, as—all coils have an intrinsic self resonance—typically at much higher frequencies (e.g. 10-40 MHz).

The second method involves connection through fast electronic switches. A non-resonant system uses an un-tuned coil. That is, no tuning capacitor is used. Instead, the RF frequency excitation is achieved by the use of fast electronic switches, such as MOSFET switches. These switches control the timing and the direction of the current flow in the coil. Turning these switches on and off at a certain pattern allows the creation of the alternating current in the coil thus producing RF irradiation. The current pattern often includes a period of positive current followed by a period of negative current, simulating a sinusoidal waveform. Repeating this pattern at a given frequency allows the generation of RF power at that frequency. Such frequency and the details of the current pattern are under the control of the switches.

As a result, in certain embodiments, these switches may need to be able to switch at the Larmor frequencies, and it could be advantageous if they were able to switch preferably significantly faster. Additionally, in certain embodiments, the switches may need to be able to handle high current and have a fast recovery time.

Figure 6:
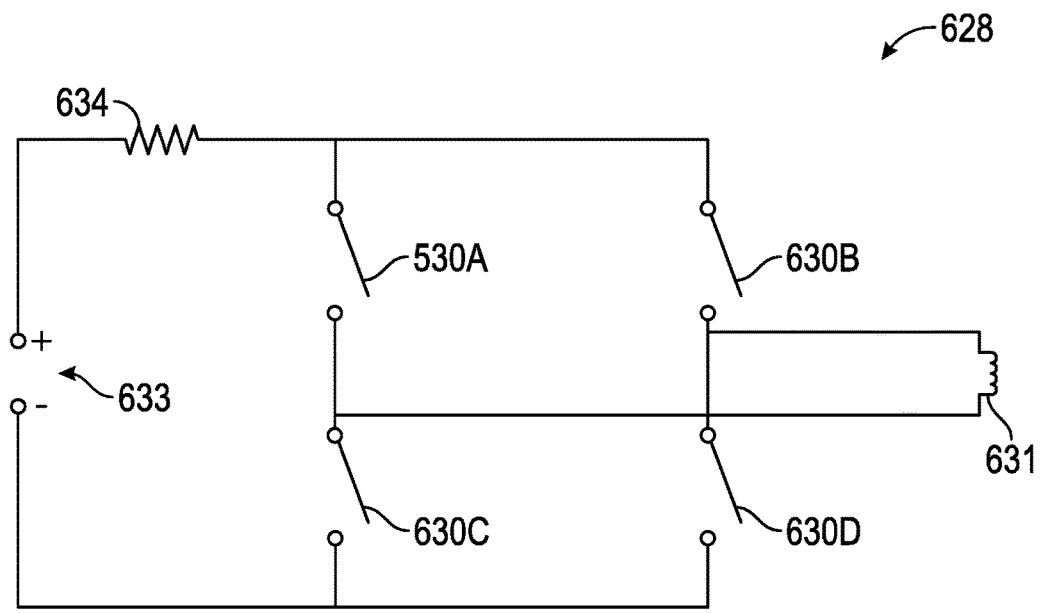
FIG. 6 is a schematic of an H-bridge for use in a non-resonant NMR logging tool, according to an example embodiment.

FIG. 6 is a schematic of an H-bridge 628 for use in a non-resonant NMR logging tool, according to an example embodiment. As shown in FIG. 6, one of the designs for a non-resonant circuit is an H-bridge 628 with the coil 631 in the middle. The circuit 628 can include a resistor 634, and the power supply for the circuit can be a battery 633. The battery 633 can drive electric current through the coil in two directions by controlling the on- and off-states of the switches. This is one of the advantages of this design to achieve a bipolar current from a single voltage source. One disadvantage is that four switches are needed.

In the example system shown in FIG. 6, there are 4 MOSFET switches, 630A-D. In the half (H) bridge design, they are turned on and off in pairs. Switches 630A and 630D are paired, as are 630B and 630C, similarly to the (t0-t1) and (t2-t3) pairs described above with reference to FIG. 2.

As an example, to generate a 250 kHz pulse in the coil, the following timings can be used: at Time=0 us, 630A and 630D for t1 are switched on. Then, 630A and 630D are switched off at the end of t1 for Δt. Then, 630B and 630C are switched on for the duration of t2. At the end of t2, 630B and 630C are switched off, and then waiting for Δt. In some embodiments, there must be some recovery time for the transients in the FETS between when 630A-630D are switched off and 630B-630C are switched on—this is Δt. Table 1 illustrates this example.

TABLE 1

| Step | Time | Operation | denoted | Cumulative Time |
|------|------|-----------|---------|-----------------|
| 1 | 0 μs | all off | | 0 μs |
| 2 | 1.1 μs | A-D on | t1 | 1.1 μs |
| 3 | 0.9 μs | A-D off | t1 + Δt | 2.0 μs |
| 4 | 1.1 μs | B-C on | t2 | 3.1 μs |
| 5 | 0.9 μs | B-C off | t2 + Δt | 4.0 μs |

From this timing, a 250 kHz frequency (1/4.0 μs) is generated in the coil.

Figure 7:
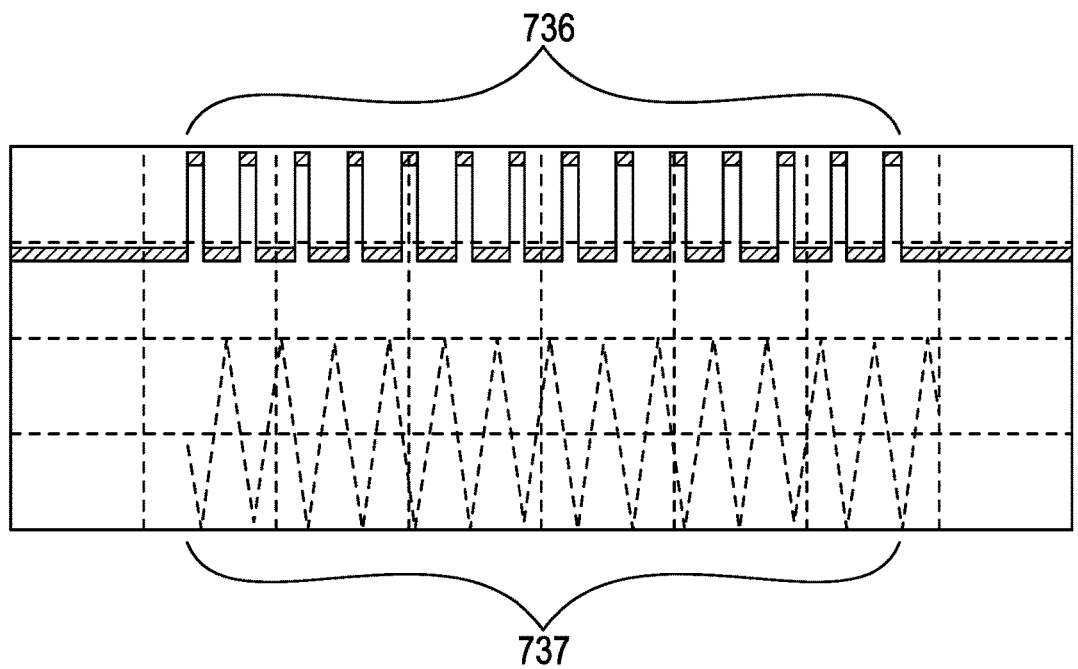
FIG. 7 is a graph of a pulse program, according to an example embodiment.

FIG. 7 is a graph of a pulse program, according to an example embodiment. FIG. 7 shows an example oscilloscope trace of the current wave pattern of an excitation pulse based on the pulse program described above. The top pulses 736 are the logic input pulses to trigger the beginning of the pulse program. This provides the start of the timing for each cycle. The trace 737 at the bottom shows the current pulses generated in the coil from the H-bridge. The full period of the wave is 4 μs thus the frequency of the wave is 250 kHz.

The rise time of the current pulses is determined by the inductance of the coil and the resistance in the circuit and it is characterized by a time constant Tr=L/R, where L is the inductance of the coil, and R is the resistance placed in series with the switches. The current is also affected by the power supply voltage. By adjusting the supply voltage, inductance and the resistance of the circuit, the current injected into the coil can be optimized.

One sequence of the example pulse program produces a positive current followed by a negative current. Repetition of the pulse program produces a train of the alternating current and the rate of the repetition determines the frequency of the RF generated. Even though the circuit is broadband, however, most of the energy of the pulse is at the repetition frequency and the power at harmonics of the switching frequency is low for the wave pattern shown in FIG. 7. Thus the efficiency of the power delivery can be good. In addition, the RF frequency may be only controlled by software to determine the timing of the pulse program, which means there may be no need to adjust the tuning and matching capacitors as for a conventional NMR circuit. This can be a significant advantage, for example, in a NMR system with a static magnetic field gradient in the magnetic field, as these multiple frequencies can correspond to different spatial locations.

The number of the repetition determines the total length of the RF pulse. This length is quite important in NMR since it determines the rotation angle of spins under the RF irradiation. The number of repetitions can be easily changed through the control software.

The relative phase of the RF pulse can also be changed easily in this example scheme. For example, consider pulse program B which follows the steps similar to the pulse program shown in FIG. 7, but shifted by half cycle: 4->5->1->2->3, instead of the pulse program: 1->2->3->4->5. This second pulse program can create a current pattern with negative current first followed by a positive current. Thus the second pulse program is a 180 degree shifted from the first pulse program. Similarly, a 90 degree phase shifted pulse is one that starts in the middle of the step 1. Phase shifting is in general dependent on the details of the pulse program and timing.

FIG. 8 is a schematic of an H-bridge 839 for use in a non-resonant NMR logging tool, according to an example embodiment. The components of FIG. 8 are similar to the components shown and described above with reference to FIG. 6. FIG. 8 further shows a battery with a constant voltage source as the power supply 840. Alternatively (or additionally) it is possible to use an electronic power source. Moreover, in some embodiments, the power supply 840 includes a modulator.

There are other switching networks that can be used. FIG. 9 is a schematic of a circuit for use in a non-resonant NMR logging tool, according to an example embodiment. The circuit of FIG. 9 includes two power supplies 943 and two switches 942A,C. In this embodiment, the inductor coil 945 will be connected to the power supplies 943 at either end, and there can be a center tap 946 from the coil to ground. In certain embodiments, the power supply 943 needs to provide both positive and negative voltage.

The operation of the two-switch 942A,C circuit of FIG. 9 can be as follows in one example. At time=0 s, switch 942A is switched on for t1. Then, switch 942A is switched off at the end of t1 for Δt. Then, switch 942C is switched on for the duration of t2. At the end of t2, switch 942C is switched off, then waiting for Δt. There may need to be some recovery time for the transients in the FETS between when switch 942A is switched off and switch 942C is switched on—this is Δt.

It is also possible to use just a single switch to connect the power supply. FIG. 10 is a schematic of a circuit for use in a non-resonant NMR logging tool, according to an example embodiment. The coil shown in FIG. 10 is connected to ground on one end and to the power supply 943 (via the switch 942) on the other. In an example embodiment, it will operate as following. At Time=0 us, switch 942A is switched on for t1. Then, switch 942A is switched off at the end of t1 for Δt. Then, switch 942A is left off for the duration of t2+Δt.

The use of a single switch would only provide a simple on/off state. Thus, the coil may only be charged with current flow for half of the cycle. In some embodiments, this can be considered an inefficient way to excite at the RF frequency since significant amount of power is dissipated at DC.

One example key in a successful detection circuit for NMR is to achieve a high degree of isolation with the power circuit while maintaining high gain and good noise performance. Certain techniques used in conventional NMR circuit can be applied with the non-resonance coil. For example, the use of two coils can be very effective. In fact, that allows much flexibility in the design of the circuit, such as using a second coil for receiver which can be a tuned circuit.

Various alternative and additional embodiments exist, as may be recognized by one of ordinary skill in the art having benefit of the present disclosure. For example, the opposite arrangement can be used too, i.e. using a tuned circuit for RF power irradiation and the second untuned coil for receiver. This configuration can be beneficial to obtain ultra-fast recovery and short dead time. Additionally, a quarter wave cable with the shunt cross diodes can be commonly used to achieve good isolation. Furthermore, a circuit made of lump components (capacitors, inductors, resisters and diodes) can be made to simulate the performance of the quarter-wave cable to achieve the isolation. Moreover, another general method used to achieve good isolation can be the use of Q-switch.

Figure 11:
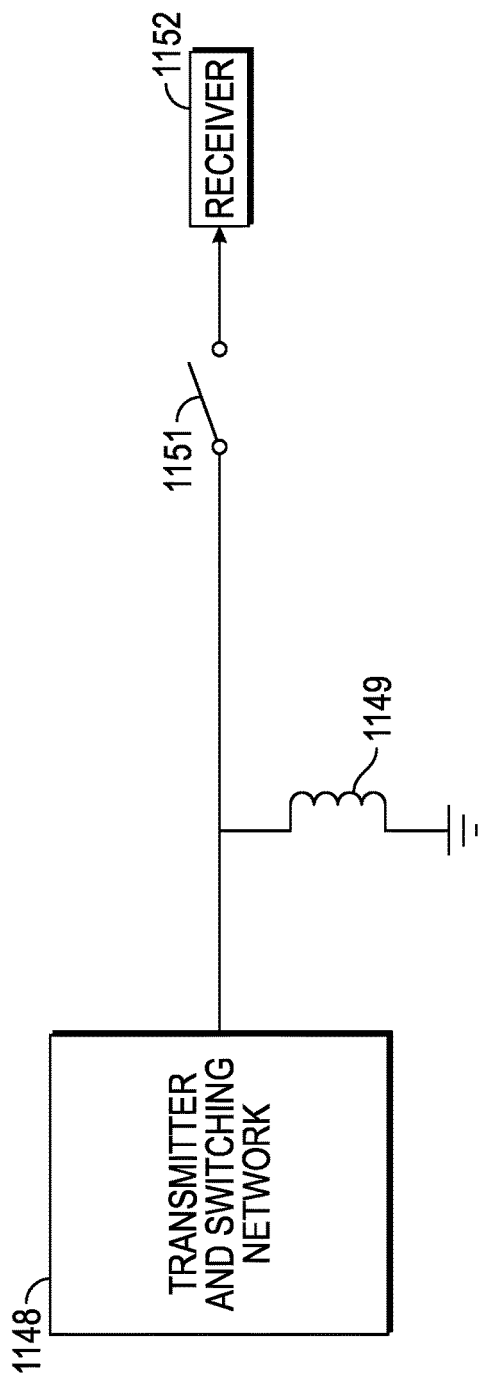
FIG. 11 is a schematic of a non-resonant NMR system, according to an example embodiment.

In addition to these coupling schemes derived from the conventional NMR circuits, the untuned circuit allows new possible coupling methods by using electronic switch. The switches can be used to switch in the receiver electronics at some point in time after the power RF amplifier is switched off. FIG. 11 is a schematic of a non-resonant NMR system, according to an example embodiment. As shown in FIG. 11, the system can include a transmitter and switching network 1148, and a switch 1151 can be disposed between the RF coil 1149 and the receiver 1152. In some embodiments, crossed diodes (not shown) may also be replaced by a switch or vice-versa.

It is possible to combine these methods into the NMR circuits in order to improve the isolations. Fast electronic switches are important for NR NMR as described earlier. The metal-oxide-semiconductor field-effect transistor (MOSFET) is a device used for amplifying or switching electronic signals. As an example, MOSFETs made by Behlke Electronic GmbH are based on the HTS (high frequency switching) family. They can be relatively easy to handle, have high reliability, low jitter and precise switching. This is in contrast to conventional high voltage switches like spark gaps, electron tubes, gas discharge tubes and mechanical switches. HTS have generally shown to have very stable switching characteristics independent of temperature and age. The switches can be turned on by a positive voltage between 2 and 10 volts, with the on-time varying between 100 ns and infinity. Significantly, they have a short recovery time of 300 ns that allows burst frequencies up to 3.3 MHz. Another important point is to have a short turn-on rise time. The HTS transistor switches from Behlke can handle up to 5000 V and 140 Amps. These are just examples of components that can be used, and there are several other companies who make suitable switches, as may be recognized by one of ordinary skill in the art having the benefit of the present disclosure.

In some embodiments, Insulated Gate Bipolar Transistors (IGBTs) can be used. IGBTs can offer a high current and low voltage drop across the bipolar transistor as well as short recovery time, low jitter and a long lifetime typical of semiconductor devices. The IGBTs typically have much longer turn off phase (e.g. 5 us) compared to the MOSFET. They offer lower burst frequencies (~1 MHz from Behlke) compared to a MOSFET. Electronic component suppliers such as Honeywell also provide similar switches.

The NMR signal often shows a narrow frequency distribution around the Larmor frequency. In a uniform magnetic field, such frequency spread is typically due to chemical shift, J-coupling, Knight shift, and quadropolar and dipolar interactions. In a non-uniform field, such as that for a logging tool, the field distribution may be so large that the RF pulses can only excite a small portion of the frequency spectrum and correspondingly a small region in space. Such excited frequency range is primarily determined by the strength of the RF magnetic field, B1, typically a few Gauss. For example, if B1=1 G, the corresponding frequency range will be 4.2 kHz. As a result, the receiver circuit and electronics need to limit its bandwidth around the Larmor frequency in order to reject the noise from outside the bandwidth and enhance sensitivity.

Figure 12:
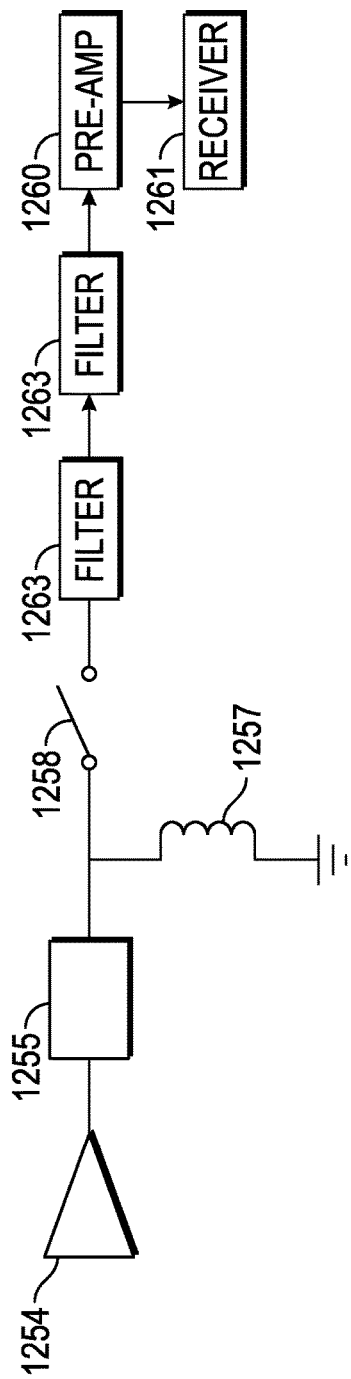
FIG. 12 is a schematic of a non-resonant NMR system, according to an example embodiment.

In conventional NMR systems, the tuned resonance circuit can function as a natural bandpass filter that rejects noise from frequencies outside the tuned resonance. However, this function can be replaced by other filters. FIG. 12 is a schematic of a non-resonant NMR system, according to an example embodiment. As shown in FIG. 12, the system can include a transmitter 1254 in communication with crossed diodes 1255, an RF coil 1257, a switch 1258, a pre-amplifier 1260, and a receiver 1261, with one or more filters 1263 between the switch 1258 and the pre-amplifier 1260. In various embodiments, the one or more filters 1263 can include a variety of types of digital or analog filters to provide a bandpass filter to reduce the noise from out of band frequencies. For example, a Chebychev filter can be used. Other filters can include Hanning, Bessel, Linkwitz-Riley, Ladder, Butterworth, Equiripple, or Elliptic filters, and/or other types of suitable filters that may be recognized by one of ordinary skill in the art having benefit of the present disclosure. In some embodiments, the use of multiple filters can be beneficial as they can help to improve the signal-to-noise ratio. As noise is digitally filtered out, there is generally an improvement in signal-to-noise ratio. Some filters, such as Butterworth and Equiripple filters, are designed to optimize signal to noise, reject interference, reject aliasing, reject artifacts, and the like.

Also, digital filtering can be used here. For example, the signal after the preamplifier (or even more stages of amplification) can be digitized through an Analog-Digital Converter (ADC) into digital form. Then digital filtering can be applied to the data by numerical calculation, such as averaging over number of data points. A simple digital Chebychev filter with a narrow bandwidth can also be easily implemented. Band pass and band cut off can also be used during various data processing stages. In certain embodiments, one important criterion for successful digital filtering is that the original data sampling rate needs to be sufficiently higher than the desired frequency bandwidth. This is often called over-sampling. Another important point is that the dynamic range of the ADC may need to be sufficient to provide the data with enough 'depth' to digitally process.

Also, it is possible to combine analog filtering with digital filtering. The analog filter can provide a broadband filter, for example, having a bandwidth of 1 MHz which could be the broadest bandwidth that will be necessary for a particular example system. Then, the digitization rate can be preset to 1 MHz and digital filtering can be used to downsample the data to the desired bandwidth (for example, 10 kHz). One of the benefits of such embodiments is that there may not be a need to adjust the analog filter and the ADC circuitry during operation. Rather, the variable bandwidth can be achieved completely by software through the digital filtering.

Figure 13:
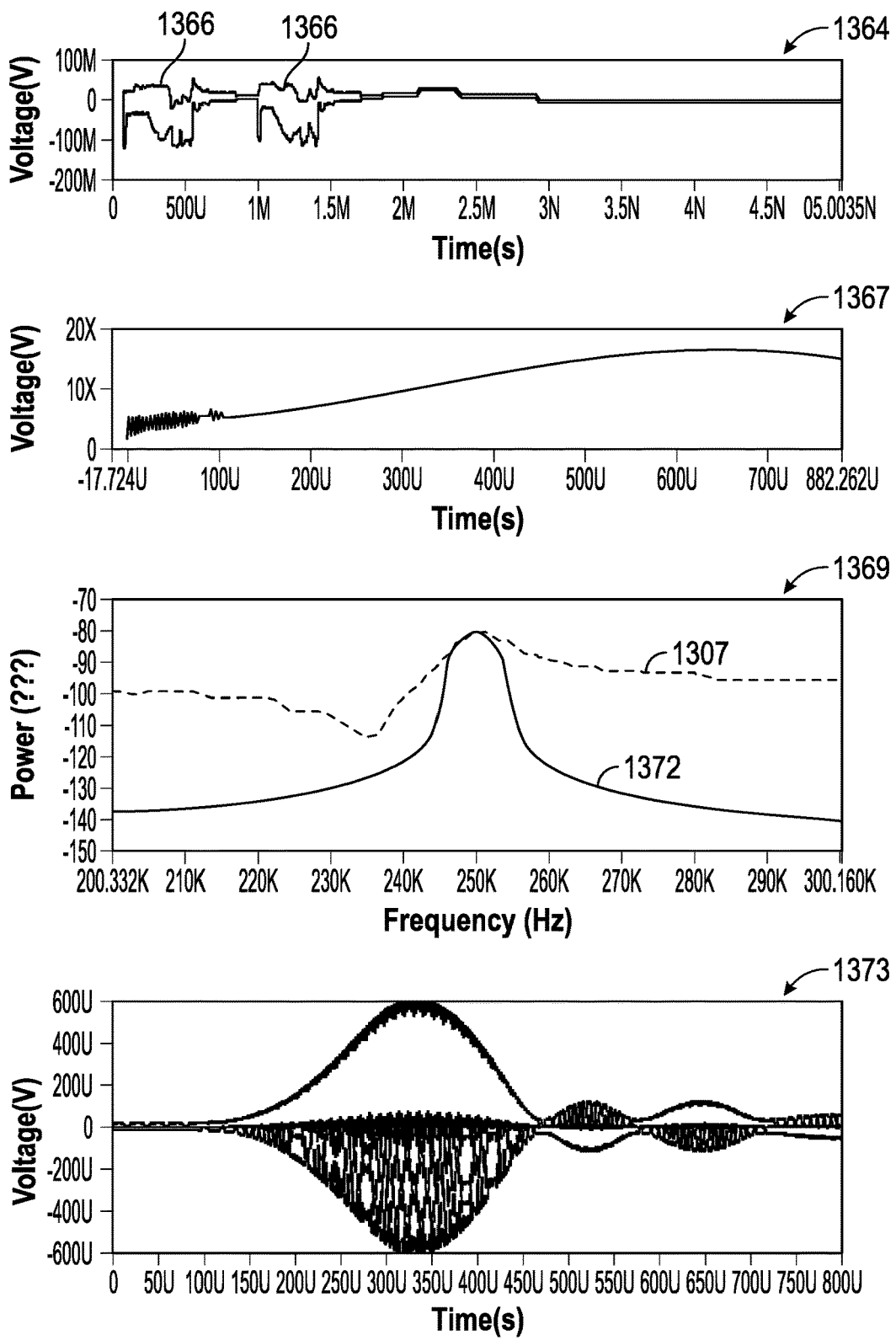
FIG. 13 is a set of graphs illustrated results from an NMR system combining analog and digital filtering, according to an example embodiment.

FIG. 13 is a set of graphs illustrated results from an NMR system combining analog and digital filtering, according to an example embodiment. For example, the filtering used to generate the graphs of FIG. 13 can include a wideband analog receive coil and a sharp digital filter. The top trace 1364 is a spin echo signal from time t=0 µs to t=300 µs. With the 90 deg and 180 deg pulses seen as the white saturated sections 1365. The second trace 1367 is a subset taken from the original top time domain data. Note that the NMR echo signal cannot be seen in this time domain data. The third trace 1369 has two curves in it. A first curve 1370 is the response of a tuned receive coil in frequency space. As can be seen, the Q, whilst very low, is centered on the frequency of interest. The second curve 1371 is a digital Chebychev 7 pole filter in frequency space. It has a very narrow bandwidth (10 kHz, centered at 250 kHz). This digital filter is then applied on the time domain data from the second trace 1367. The result is the time domain trace 1373 on the bottom. This now shows the spin echo.

With an untuned coil, the NMR circuit may not impose a restriction on the range of operating frequency and bandwidth. This can be a very important advantage for multiple-frequency NMR to switch to different excitation and detection frequencies with broadband hardware. In conventional NMR, when multiple frequencies are used, special NMR probes are needed to pre-adjust the desired set of frequencies, e.g. the frequencies corresponding to hydrogen (proton), carbon-13, and nitrogen-15. These probes often employ several coils for different frequency channels and additional capacitors and inductors to achieve different resonance frequencies and mutual isolation. In NMR logging applications, different frequencies are used to register spatial regions at different distance from the tool, such as the multiple shell measurements by MR SCANNER, an NMR tool of the assignee of the present disclosure. Different sets of capacitors can be used in order to tune the coil to the desired frequencies and a set of mechanical relays is used to select the capacitor set to achieve the specific tuning frequency.

With a non-resonance NMR circuit, the desired NMR frequency can simply be selected from the control software for both the excitation and detection (e.g. using digital filtering) without hardware adjustment. This will greatly simplify execution of multiple-frequency NMR and improve the robustness of the NMR hardware.

There are many ways to combine the techniques discussed earlier for such multiple frequency NMR system. One implementation is to have digital filtering at each specific frequency with a non-resonant receive coil. This avoids the need to retune the receiver for each frequency. Alternatively, an array of tuned LC circuits that are switched to when receiving can be used. Since these are low power, they do not present the same difficulties faced in downhole NMR tools—that is, they may not have to have large amounts of power passing through them during the excitation stage. Thus, each LC circuit can act just like an analog filter for each frequency. Using a variable lumped element PI network in this section might also be possible.

Other filters include cascaded integrator-comb (CIC), a finite impulse response FIR and an infinite impulse response (IIR) filters. A (FIR) filter is a type of a digital filter. The impulse response, the filter's response to a Kronecker delta input, is finite because it settles to zero in a finite number of sample intervals. This is in contrast to (IIR) filters, which have internal feedback and may continue to respond indefinitely. The impulse response of an Nth-order FIR filter lasts for N+1 samples, and then dies to zero.

An FIR filter is used in a wide array of applications, and can be used in multi-rate processing in conjunction with an interpolator or decimator. CIC filters have low pass frequency characteristics while FIR filters can have low-pass, high-pass, or band-pass frequency characteristics. CIC filters use only addition and subtraction and are used in multi-rate processing. FIR filters use addition, subtraction, but most FIR filters also require multiplication. CIC filters have a specific frequency roll-off, while low pass FIR filters can have an arbitrarily sharp frequency roll-off.

CIC filters in general can be much more economical than general FIR filters, but tradeoffs are involved. In cases where only a small amount of interpolation or decimation are needed, FIR filters generally have an advantage. However, when rates change by a factor of 10 or more, achieving a useful FIR filter anti-aliasing stop band requires exponentially increasing numbers of FIR taps.

Figure 14:
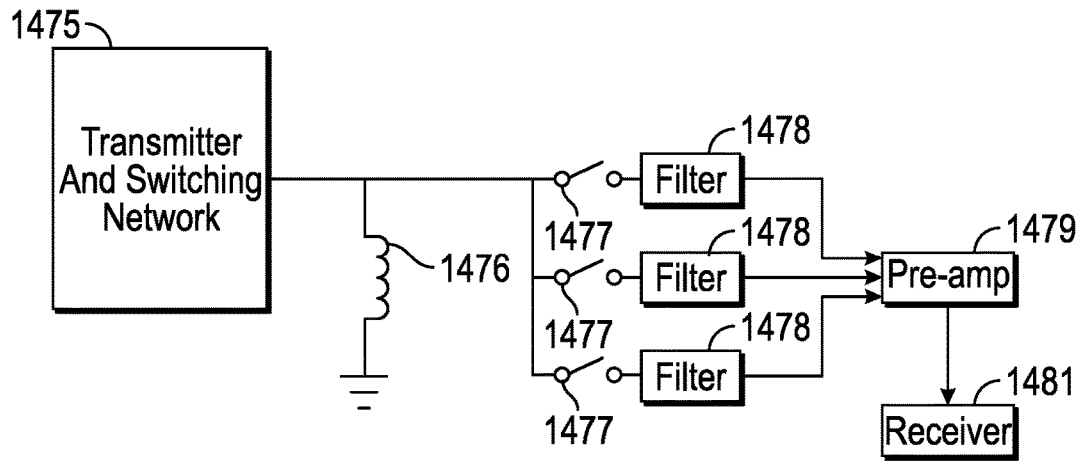
FIG. 14 is a schematic of a non-resonant NMR system, according to an example embodiment.

FIG. 14 is a schematic of a non-resonant NMR system, according to an example embodiment. As shown in FIG. 14, the system can include a transmitter and switching network 1475, an rf coil 1476, and can use filters 1478A-C in parallel with switches 1477A-C to switch between the filters 1478A-C. In the illustrated embodiment, the filters 1478 are designed to be bandpass filters. A bandpass filter allows signals of some specific range of frequency to pass through. The multiple filters 1478 in this design can be set to different frequency bands and each is designed to match a desired NMR frequency. For example, Filter 1 can be designed to allow 1 MHz signal; Filter 2 can be designed to allow 0.75 MHz signal; and Filter 3 can be designed to allow 0.5 MHz signal. These frequencies correspond to the NMR frequencies of an example NMR tool. In some embodiments, there can also be multiple pre-amps and receivers, with one set connected to each filter.

Figure 15:
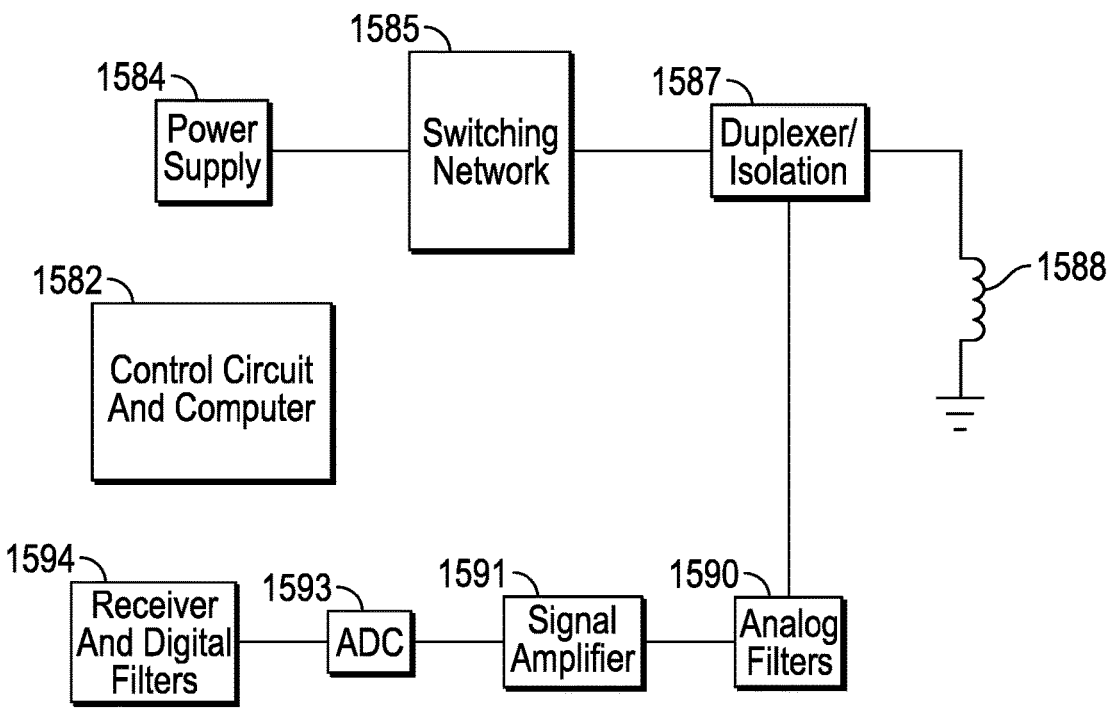
FIG. 15 is a schematic diagram of a system with non-resonant excitation and non-resonant detection for use with an NMR system, according to an example embodiment.

Schematics for some of the example embodiments disclosed herein are shown below. FIG. 15 is a schematic diagram of a system with non-resonant excitation and non-resonant detection for use with an NMR system, according to an example embodiment. As shown in FIG. 15, an NMR system can include a control circuit and computer 1582 for controlling the system. The system can further include a power supply 1584 in communication with a switching network 1585, which is in turn in communication with duplexer 1587. The duplexer 1587 is connected to a coil 1588 that can function as an excitation (transmitter) coil as well as a detection (receiver) coil. The coil 1588 then can be connected to ground. The duplexer 1587 also can maintain a connection with one or more analog filters 1590, in turn in connection with a signal amplifier 1591, an analog to digital converter 1593, and a receiver and digital filter 1594.

Figure 16:
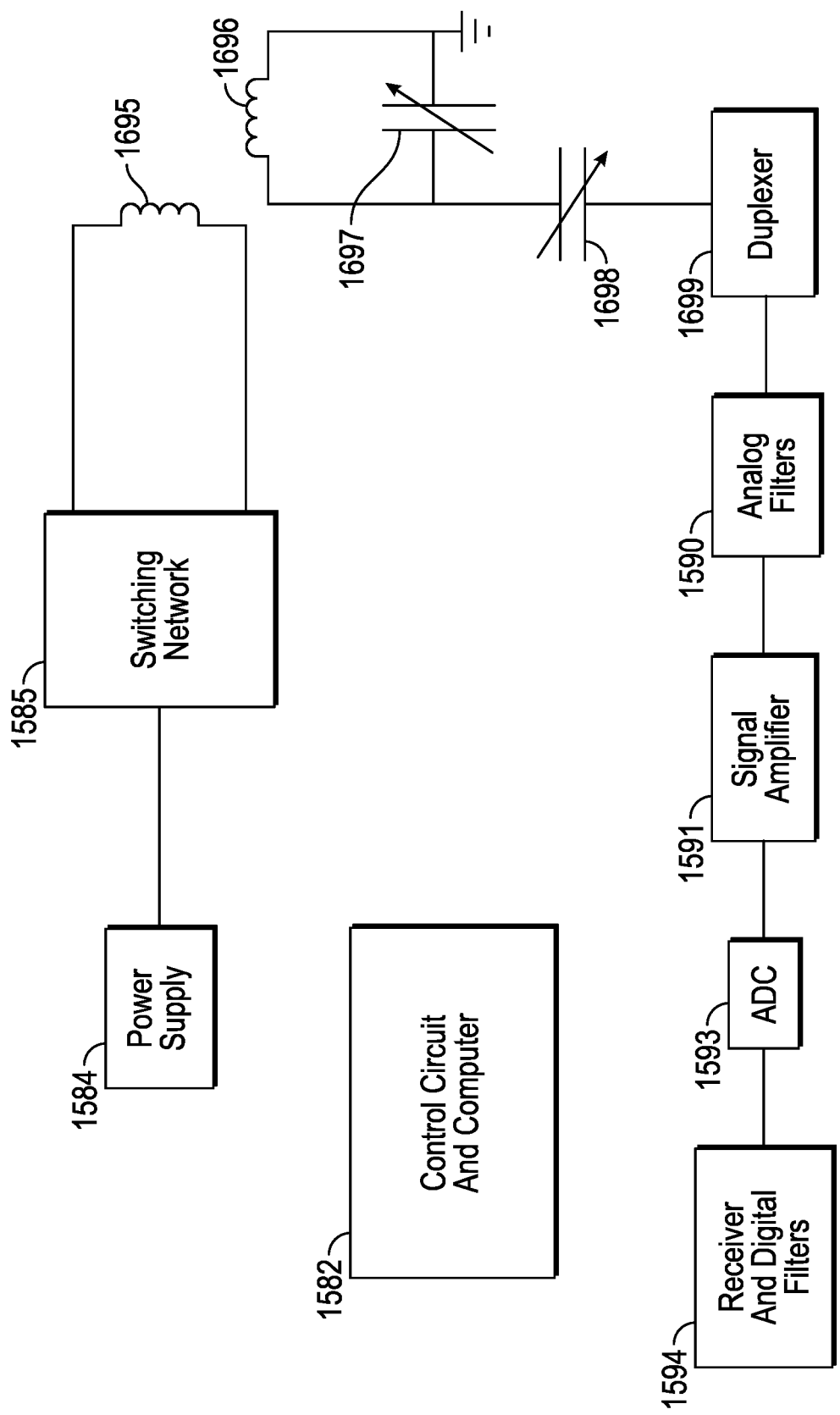
FIG. 16 is a schematic diagram of a system with non-resonant excitation and resonant detection for use with an NMR system, according to an example embodiment.

FIG. 16 is a schematic diagram of a system with non-resonant excitation and resonant detection for use with an NMR system, according to an example embodiment. The NMR system can include several of the components described above with reference to the system of FIG. 15, such as the control circuit and computer 1582, the power supply 1584, the switching network 1585, analog filters 1590, signal amplifiers 1591, analog to digital converter 1593, and the receiver and digital filters 1594. One difference between the two systems is that the system of FIG. 16 includes two separate coils—one excitation coil 1695 in communication with the switching network, and one detection coil 1696 in communication with a tuning capacitor 1697 and matching capacitor 1698 to control the frequencies of operation. The matching capacitor 1698 then may be in communication with a duplexer 1699, which in turn can be in communication with the analog filters 1590. As may be recognized by one of ordinary skill in the art having benefit of the present disclosure, in many embodiments, many of the components described herein—such as the analog filters 1590—may or may not be required and/or beneficial. When considering whether to use an analog filter 1590, for example, one determiner can be the Signal to Noise Ratio obtained. In embodiments where there is too much noise, an analog filter 1590 can be used to reduce the noise. Another consideration might be for processing power, as some digital filters can use a significant amount of memory. An analog filter 1590 can be a piece of hardware and hence may not have any "computational cost". Analog filters 1590 may be necessary for noise rejection, and anti-aliasing when there is an analog-to-digital converter 1593.

As to the example methods and steps described in the embodiments presented previously, they are illustrative, and, in alternative embodiments, certain steps can be performed in a different order, in parallel with one another, omitted entirely, and/or combined between different example methods, and/or certain additional steps can be performed, without departing from the scope and spirit of the invention. Accordingly, such alternative embodiments are included in the invention described herein. For example, although many of the embodiments described above relate to downhole logging tools, the concepts such as non-resonant circuits and probes need not be limited to downhole logging uses. In various example embodiments, the non-resonant circuits and other components can be used with NMR and/or resistivity devices to measure samples (e.g., samples in a lab, samples in a refinery, etc.).

Additionally, although some of the disclosure specifically refers to drill pipe conveyance tools, as one of ordinary skill in the art may recognize with the benefit of the present disclosure, certain aspects of the foregoing disclosure could apply to tools and toolstrings used in wireline, logging-while-drilling and/or measuring-while-drilling applications, or other methods of conveyance, in addition.

Certain aspects of the disclosure can comprise a computer program that embodies the functions described herein and illustrated in the flow charts. However, it should be apparent that there could be many different ways of implementing the invention in computer or algorithmic programming, and the invention should not be construed as limited to any one set of program instructions. Further, a skilled programmer would be able to write such a program to implement an embodiment of the disclosed invention based on the flow charts and associated description in the application text. Therefore, disclosure of a particular set of program code instructions is not considered necessary for an adequate understanding of how to make and use the invention.

The invention can be used with computer hardware and software that performs the methods and processing functions described above. Specifically, in describing the functions, methods, and/or steps that can be performed in accordance with the invention, any or all of these steps can be performed by using an automated or computerized process. As will be appreciated by those skilled in the art, the systems, methods, and procedures described herein can be embodied in a programmable computer, computer executable software, or digital circuitry. The software can be stored on computer readable media. For example, computer readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

Although specific embodiments of the invention have been described above in detail, the description is merely for purposes of illustration. Various modifications of, and equivalent steps corresponding to, the disclosed aspects of the example embodiments, in addition to those described above, can be made by those skilled in the art without departing from the spirit and scope of the invention defined in the following claims, the scope of which is to be accorded the broadest interpretation so as to encompass such modifications and equivalent structures.

What is claimed is:

1. A non-resonant magnetic resonance (MR) device for transmitting radio frequency pulses, the device comprising:
   an untuned coil for transmitting the radio frequency pulses;
   a circuit comprising:
      a power supply; and
      a plurality of switches that selectively couple and decouple the coil with the power supply, wherein the circuit is configured to alternatingly couple and decouple the coil with the power supply at a frequency selected to generate the radio frequency pulses.

2. The device of claim 1, wherein the power supply powers the coil when at least one of the plurality of switches couples the coil to the power supply.

3. The device of claim 1, wherein the plurality of switches comprises a plurality of transistors.

4. The device of claim 3, wherein the plurality of switches are arranged in an H-bridge and the circuit generates an alternating current within the coil using the H-bridge.

5. The device of claim 1, wherein the device is part of a wellbore logging tool.

6. The device of claim 1, wherein the circuit generates the radio frequency pulses without using a tuning capacitor.

7. A method for transmitting radio frequency pulses, the method comprising:
   coupling and decoupling a power supply of a circuit with an untuned coil a plurality of times to generate a radio frequency pulse.

8. The method of claim 7, further comprising repeating the coupling and decoupling a plurality of times to generate a plurality of radio frequency pulses that are each separated from adjacent radio frequency pulses.

9. The method of claim 7, wherein the coupling and decoupling are performed using a plurality of transistors.

10. The method of claim 7, further comprising
    applying the radio frequency pulse to a subterranean formation.

11. A nuclear magnetic resonance logging tool, comprising:
- an untuned coil for transmitting the radio frequency pulses into the formation;
- a circuit comprising:
    - a power supply; and
    - a plurality of switches that selectively couple and decouple the coil with the power supply, wherein the circuit is configured to alternatingly couple and decouple the coil with the power supply at a frequency selected to generate the radio frequency pulses.

12. The method of claim 1, wherein the coil comprises a non-resonant excitation coil.

13. The method of claim 1, wherein the coil comprises a non-resonant detection coil.

14. The method of claim 7, wherein the circuit generates the radio frequency pulses without using a tuning capacitor.

15. The method of claim 7, wherein the circuit comprises a plurality of switches arranged in an H-bridge and the circuit generates an alternating current within the coil using the H-bridge.

16. The tool of claim 11, wherein the circuit generates the radio frequency pulses without using a tuning capacitor.

17. The tool of claim 11, wherein the plurality of switches are arranged in an H-bridge and the circuit generates an alternating current within the coil using the H-bridge.

* * * * *